United States Patent
Marsal Barril et al.

(10) Patent No.: US 9,441,274 B2
(45) Date of Patent: Sep. 13, 2016

(54) IN VITRO METHOD AND KIT FOR PROGNOSIS OR PREDICTION OF RESPONSE BY PATIENTS WITH RHEUMATOID ARTHRITIS TO TREATMENT WITH TNF-αFACTOR BLOCKING AGENTS

(75) Inventors: Sara Marsal Barril, Barcelona (ES); Antonio Julia Cano, Barcelona (ES)

(73) Assignee: FUNDACIO INSTITUT DE RECERCA DE L'HOSPITAL UNIVERSITARI VALL D'HEBRON, Barcelona (ES)

( * ) Notice: Subject to any disclaimer, the term of this patent is extended or adjusted under 35 U.S.C. 154(b) by 606 days.

(21) Appl. No.: 13/120,445

(22) PCT Filed: Sep. 18, 2009

(86) PCT No.: PCT/ES2009/070388
§ 371 (c)(1),
(2), (4) Date: Jul. 8, 2011

(87) PCT Pub. No.: WO2010/034864
PCT Pub. Date: Apr. 1, 2010

(65) Prior Publication Data
US 2011/0263449 A1 Oct. 27, 2011

(30) Foreign Application Priority Data
Sep. 24, 2008 (ES) ................................. 200802713

(51) Int. Cl.
*C40B 30/04* (2006.01)
*C12Q 1/68* (2006.01)

(52) U.S. Cl.
CPC ....... *C12Q 1/6883* (2013.01); *C12Q 2600/106* (2013.01); *C12Q 2600/158* (2013.01)

(58) Field of Classification Search
CPC .......... C12Q 1/6883; C12Q 2600/106; C12Q 2600/158
USPC ........................................ 435/6.1, 6.11, 6.12
See application file for complete search history.

(56) References Cited

U.S. PATENT DOCUMENTS
2007/0275406 A1 11/2007 Hakonarson et al.

FOREIGN PATENT DOCUMENTS
WO 2008150491 A1 12/2008

OTHER PUBLICATIONS

Nelson et al.; HLA antigens in Tlingit Indians with rheumatoid arthritis; Tissue Antigens; vol. 40; No. 2; pp. 57-63; Aug. 1992; full text.*
Lequerré et al.; Gene profiling in white blood cells predicts infliximab responsiveness in rheumatoid arthritis; Arthritis Research & Therapy; vol. 8; No. 4; R105; published Jul. 3, 2006.*
Sugihara et al.; Effects of Infliximab Therapy on Gene Expression Levels of Tumor Necrosis Factor alpha, Tristetraprolin, T Cell Intracellular Antigen 1, and Hu Antigen R in Patients With Rheumatoid Arthritis; Arthritis & Rheumatism; vol. 56, No. 7, pp. 2160-2169; published online Jun. 28, 2007.*
Lindberg et al.; Effect of infliximab on mRNA expression profiles in synovial tissue of rheumatoid arthritis patients; Arthritis Research & Therapy; vol. 8; No. 6; R179; published Nov. 29, 2006.*
GPL6884; Illumina HumanWG-6 v3.0 expression beadchip; http://www.ncbi.nlm.nih.gov/geo/query/acc.cgi?acc=GPL6884; submitted May 21, 2008; pp. 1-3 and 2813.*
Williams R. C. et al. "Meta-analysis reveals association between most common class II haplotype in full-heritage Native Americans and rheumatoid arthritis" Human immunology, vol. 42, pp. 90-94, Jan. 1995.
Nelson J. L. et al. "HLA antigens in Tlingit Indians with rheumatoid arthritis," Tissue Antigens, vol. 40, pp. 57-63, Aug. 1992__Abstract.

* cited by examiner

*Primary Examiner* — Antonio Galisteo Gonzalez
(74) *Attorney, Agent, or Firm* — Tristan A. Fuierer; Moore & Van Allen, PLLC (57) ABSTRACT

In vitro method and kit for prognosis or prediction of the response of rheumatoid patients to treatment with TNF-α factor blocking agents, which comprises determining, in a blood sample from said patients, the expression level of at least one of the eight genes selected from the group: HLA-DRB3, EAT2, GNLY, CAMP, SLC2A3, IL2RB, MXD4 and TLR5 or combinations thereof and comparing said expression level to the expression values obtained from responsive and non-responsive patients who showed responsiveness to the treatment and those who showed non-responsiveness thereto.

10 Claims, 9 Drawing Sheets

CAMP

SEQUENCE LISTING

<160> NUMBER OF SEQ ID NOS: 8

<210> SEQ ID NO 1
<211> LENGTH: 50
<212> TYPE: DNA
<213> ORGANISM: Artificial Sequence
<220> FEATURE:
<223> OTHER INFORMATION: Synthetic Construct

<400> SEQUENCE: 1
tcccgcctgg ctgttattct tccacgagag agggctttct caggacctag        50

<210> SEQ ID NO 2
<211> LENGTH: 50

```
<212> TYPE: DNA
<213> ORGANISM: Artificial Sequence
<220> FEATURE:
<223> OTHER INFORMATION: Synthetic Construct

<400> SEQUENCE: 2
gtgagatttg gggtcacagc aatttatggc tactattccc tgggtctggt       50

<210> SEQ ID NO 3
<211> LENGTH: 50
<212> TYPE: DNA
<213> ORGANISM: Artificial Sequence
<220> FEATURE:
<223> OTHER INFORMATION: Synthetic Construct

<400> SEQUENCE: 3
ctacaggtcc cctctgagcc ctctcacctt gtcctgtgga agaagcacag       50

<210> SEQ ID NO 4
<211> LENGTH: 50
<212> TYPE: DNA
<213> ORGANISM: Artificial Sequence
<220> FEATURE:
<223> OTHER INFORMATION: Synthetic Construct

<400> SEQUENCE: 4
agagtcctag tgtgtgccct accctggctc aggcttctgg gctctgagaa       50

<210> SEQ ID NO 5
<211> LENGTH: 50
<212> TYPE: DNA
<213> ORGANISM: Artificial Sequence
<220> FEATURE:
<223> OTHER INFORMATION: Synthetic Construct

<400> SEQUENCE: 5
atcatgtgaa cccgggacgc aggggttgca gtgagcggag atcgcatcat       50

<210> SEQ ID NO 6
<211> LENGTH: 50
<212> TYPE: DNA
<213> ORGANISM: Artificial Sequence
<220> FEATURE:
<223> OTHER INFORMATION: Synthetic Construct

<400> SEQUENCE: 6
ctgaatgttt cagaccacaa ggggctccac acctttgctg tgtgttctgg       50

<210> SEQ ID NO 7
<211> LENGTH: 50
<212> TYPE: DNA
<213> ORGANISM: Artificial Sequence
<220> FEATURE:
<223> OTHER INFORMATION: Synthetic Construct

<400> SEQUENCE: 7
ggccacctgt ccaccgtgtg ggccgtgctg tgtccttatg tcattgtaat       50

<210> SEQ ID NO 8
<211> LENGTH: 50
<212> TYPE: DNA
<213> ORGANISM: Artificial Sequence
<220> FEATURE:
<223> OTHER INFORMATION: Synthetic Construct

<400> SEQUENCE: 8
```

```
cagaggcttt gtacagaaac agcagtattt gaggtggcct gaggatctcc          50
```

IN VITRO METHOD AND KIT FOR PROGNOSIS OR PREDICTION OF RESPONSE BY PATIENTS WITH RHEUMATOID ARTHRITIS TO TREATMENT WITH TNF-αFACTOR BLOCKING AGENTS

CROSS-REFERENCE TO RELATED APPLICATIONS

This application is filed under the provisions of 35 U.S.C §371 and claims the priority of International Patent Application No. PCT/ES2009/070388 filed on 18 Sep. 2009 entitled "In Vitro Method and Kit for Prognosis or Prediction of Response by Patients with Rheumatoid Arthristis to Treatment with TNF-α Factor Blocking Agents" in the name of Antonio JULIÁ CANO, et al., which claims priority to Spanish Patent Application No. P200802713 filed on 24 Sep. 2008, both of which are hereby incorporated by reference herein in their entirety.

FIELD OF THE INVENTION

The present invention relates to an in vitro method (hereinafter, method of the invention) for prognosis or prediction of the response of rheumatoid arthritis patients to treatment with tumour necrosis factor alpha (TNF-α) blocking agents, such as for example infliximab or adalimumab. Therefore, the present invention may be encompassed within the field of personalised medicine, rheumatology or human genetics as a field that studies genetics-based diseases.

STATE OF THE ART

Rheumatoid arthritis (RA) is one of the most widespread autoimmune diseases in the world (worldwide prevalence ~1%). RA leads to the chronic inflammation of synovial articulations and to the development of progressive articular damage which can give rise to significant functional incapacity. Additionally, RA is a very heterogeneous and complex disease in all its aspects, including both its clinical manifestations and variability of response to different therapies.

The intense research carried out in recent years has led to the identification of several treatments for controlling RA. In the last decade, TNF-α-inhibiting biological treatments have undergone greater development with respect to RA control, in comparison to therapies based on DMARD (disease-modifying anti-rheumatic drugs).

At present, infliximab is one of the most frequently used therapies in RA treatment. Infliximab is a chimeric monoclonal antibody (IgG) derived from a recombinant DNA of human and murine origin, which binds to and neutralises TNF-α, interrupting the sequential cascade of activation of the inflammatory pathways mediated by this cytokine.

However, there is a percentage of patients do not respond to treatment with TNF-α factor blocking agents and must be transferred to alternative therapies. On the other hand, the methods for prognosis or prediction of which patients can benefit from this treatment and their differentiation from patients who do not respond to said treatment and will be focalised towards alternative therapies, which are becoming increasingly necessary to undertake the challenge posed by individualised medicine.

The document ["*Gene profiling in white blood cells predicts infliximab responsiveness in rheumatoid arthritis*," Thierry Lequerré et al.] discloses the study of the gene expression profile (by quantifying the mRNA level) in peripheral mononuclear cells (PBMCs) (which implies a fraction less than 60% of the blood cells), as a base for predicting the response of RA patients to infliximab. A group of genes correlated with treatment response was determined. The genes studied are shown in different tables and figures in this document, the most complete list being shown in Table 4.

The document ["*Effect of infliximab therapy on gene expression levels of tumour necrosis factor alpha, tristetraprolin, T cell intracellular antigen 1, and Hu antigen R in patients with rheumatoid arthritis*," Sugihara, Makoto et al.] identified parameters that can predict the effectiveness of anti-TNF-α therapy in RA patients. To this end, TNF-α, TTP, TIA-1 and HuR gene expression levels were analyzed and it was concluded that the difference in ABP (TTP, TIA-1 and HuR) gene expressions can affect TNF-α gene expression. A high TIA-1:HuR expression ratio can be related to patient response to treatment with infliximab.

The document ["*Effect of infliximab on mRNA expression profiles in synovial tissue of rheumatoid arthritis patients*," Johan Lindberg et al.] discloses the examination conducted on the gene expression profile of RA patients for researching whether said profiles can be used to predict patient response to treatment with infliximab. To this end, the expression profile of a series of genes such as MMP-3 and others mentioned on page 5 was studied (left column, second paragraph).

None of the documents found in the state of the art describe any of the eight genes, the expression level of which is analysed in the present invention: HLA-DRB3 (NCBI: 3125), EAT2 (NCBI: 117157), GNLY (NCBI: 10578), CAMP (NCBI: 820), SLC2A3 (NCBI: 6515), IL2RB (NCBI: 3560), MXD4 (NCBI: 10608) and TLR5 (NCBI: 7100). Therefore, there is no evidence in the state of the art related to the use of the eight aforementioned genes which, as explained in the description of the invention, have been specifically selected in the present invention by means of an exhaustive screening process carried out among thousands of genes.

It must be noted that, although in the present invention, the optimum predictor model is the one which considers the expression of the aforementioned set of eight genes as a whole, each of these eight genes has predictive potential by itself. Therefore, any of the eight aforementioned genes, any sub-combination of the eight genes with a number of genes ≥2 or the set of eight genes in its entirety can be used in the method of the invention, with sufficient indications of effectiveness.

Additionally, another important difference of the method of the invention with respect to the methods disclosed in the state of the art relate to the nature of the biological sample used to analyse the gene expression. In the present invention and contrary to the state of the art, mRNA is isolated from whole blood and analysed, without carrying out any prior fractioning. Therefore, the expression profile includes the whole blood cell population. This aspect acquires importance on taking into account that each cell type or population can have different associated gene expression profiles.

The type of sample taken in the present invention (whole blood) makes the method much less invasive for the patient and constitutes another difference with respect to some of the known methods wherein synovial biopsies are performed for sample extraction.

DESCRIPTION OF THE INVENTION

Brief Description of the Invention

The present invention relates to an in vitro method for prognosis or prediction of the response of rheumatoid arthritis patients to treatment with TNF-α factor blocking agents, which comprises determining at least one of the eight genes selected from the group: HLA-DRB3 (NCBI: 3125), EAT2 (NCBI: 117157), GNLY (NCBI: 10578), CAMP (NCBI: 820), SLC2A3 (NCBI: 6515), IL2RB (NCBI: 3560), MXD4 (NCBI: 10608) and TLR5 (NCBI: 7100) in a blood sample from said patients and by quantification of the transcriptional expression level (mRNA); and comparison of said expression level with respect to the expression values previously obtained from responsive and non-responsive patients who showed responsiveness to the treatment and those who showed non-responsiveness thereto.

Additionally, the present invention relates to a kit for prognosis or prediction of the response to treatment of rheumatoid arthritis patients with TNF-α factor blocking agents, which comprises at least one probe that hybridises with at least one of the nucleotide sequences of the following genes: HLA-DRB3 (NCBI: 3125), EAT2 (NCBI: 117157), GNLY (NCBI: 10578), CAMP (NCBI: 820), SLC2A3 (NCBI: 6515), IL2RB (NCBI: 3560), MXD4 (NCBI: 10608) and TLR5 (NCBI: 7100).

The probes comprised in the kit are characterised by sequences SEQ ID NO: 1-8.

As can be observed in FIGS. 2-9, it must be taken into account that the genes over-expressed in non-responsive patients before starting the treatment are: MXD4, HLA-DRB3, IL2RB, EAT2, GNLY and the genes over-expressed in responsive patients before starting the treatment are: TLR5, CAMP and SLC2A3.

On the other hand, it must be mentioned that genes HLA-DRB3, EAT2, GNLY, CAMP, IL2RB and TLR5 are all related to the immune response.

Therefore, the technical problem solved by the present invention relates to an in vitro model for prognosis or prediction of the response to treatment with tumour necrosis factor-alpha TNF-α blocking agents (such as for example infliximab or adalimumab) by rheumatoid arthritis patients, based on whole blood samples (i.e. comprising 100% of the cell populations present therein and not only PBMC cells), which is alternative to those currently existing in the state of the art (the genes analysed are different to those used in the methods disclosed), simple (based on the analysis of a small number of genes) and minimally invasive for the patient (does not require biopsies).

Predicting response of RA patients to the treatment will be useful in two main aspects:

1. Prediction of non-responsive patient to treatment with TNF-α factor blocking agents: this will allow the patient to be directed towards alternative treatments to TNF-α factor blocking without the need to apply, as a preliminary treatment, TNF-α factor blocking therapy. Some of the possible side effects from treatment with TNF-α factor blocking agents are the following (Ledingham et al. Rheumatology 2005):
a. Serious infections excluding tuberculosis.
b. Tuberculosis.
c. Lymphomas.
d. Appearance of Systemic Erythematous Lupus.
e. Heart failure.
f. Demyelination and neurological complications.
g. Haematological complications.

2. Prediction of responsive patient to TNF-α factor blocking agents: this tool is very useful for starting the treatment at an early stage, as in the specific case of RA it has been proven that treatment during the early stages of the disease can be very effective in preventing the progression of the articular erosions.

Based on the observation of FIGS. 2-9, it can be clearly inferred that those genes over-expressed in non-responsive patients prior to starting the treatment are: MXD4, HLA-DRB3, IL2RB, EAT2 and GNLY, and the genes over-expressed in responsive patients prior to starting the treatment are: TLR5, CAMP and SLC2A3.

DETAILED DESCRIPTION OF THE INVENTION

The present invention relates to an in vitro method and kit for prognosis and prediction of the response of rheumatoid arthritis patients to treatment with TNF-α factor blocking agents, which comprises determining, in a blood sample of said patients by means of mRNA level quantification, the expression level of at least one of the eight genes selected from the previously indicated group and comparing said expression level to the expression levels previously obtained from responsive and non-responsive patients who showed responsiveness to the treatment and those who showed non-responsiveness thereto.

Selection of Patients

Between January 2005 and June 2007, those patients defined as having a DAS28 index (Disease Activity Score>3.2) and therefore active RA, were selected for treatment with infliximab.

The criteria for including the patients in the therapy were:
1. Fulfilment of 1987 ACR (American College of Rheumatology) criteria for RA diagnosis.
2. Tolerance to treatment with methotrexate ($\leq$20 mg/week).
3. Able to receive prednisolane (dose$\leq$10 mg/day) and treatment with NSAID (Non-Steroidal Anti-Inflammatory Drug).
4. The doses of methotrexate, glucocorticoids and NSAID must remain stable during the four weeks prior to treatment.
5. Not have received any other DMARD during the four weeks prior to inclusion in the study.
6. All the standard criteria defined for including the patients in treatment with infliximab must be fulfilled.

The criteria for excluding patients from the treatment are:
1. Patients with hepatitis B (active or inactive).
2. All the standard criteria defined for excluding the patients in treatment with infliximab must be fulfilled.

Clinical Procedures for Evaluating the Response to Infliximab

At the time of the first infusion (week zero), in the second week and in the fourteenth week, clinical variables corresponding to the activity of the disease were recorded. These variables include: number of painful articulations, number of swollen articulations, C-reactive protein (CRP), globular sedimentation speed (GSS) and HAQ (Heath Assessment Questionnaire).

The response to therapy with infliximab was evaluated based both on EULAR (European League Against Rheumatism) response criteria and ACR (American College of Rheumatology) response criteria.

EULAR defines the criteria based on two variables:
1. The variation in the activity score DAS28 (Disease Activity Score).
2. The initial result of DAS (Disease Activity Score).

ACR defines the response level on the basis of the percentage of reduction in several clinical variables (ACR50 is equivalent to a reduction of 50% in the aforementioned clinical variables).

In the present invention, a variable binary response was used wherein non-responsive patients were classified as non-responsive in both systems (i.e. "Poor Response" in EULAR and "ACR0" in ACR). Therefore, "Moderate" EULAR, "Good" EULAR, "ACR20", "ACR50" and "ACR70" were included in the group of patients who responded to the treatment.

Blood Collection and RNA Extraction

The blood samples for RNA extraction were taken from the patients before starting treatment with infliximab. One of the factors that influence the RNA profile extracted from the blood cells is the time of day when the sample is taken. For the purpose of minimising this source of variability, all the blood samples were taken between 8:30-9:30 a.m.

The "PAXGene" (PreAnalytix, Switzerland) system was used in the present study for immediate preservation of RNA from whole blood samples. This system uses a RNA-preserving agent contained in the same blood extraction tube and, therefore, the blood profiles obtained are representative of the in vivo conditions. All of the "PAXGene" tubes were stored frozen at $-80°$ C. until isolating the RNA. The RNA was extracted using a total "PAXGene" isolation kit (Qiagen, USA). Finally, the RNA quality of all the samples was evaluated using the "BioAnalyzer" (Agilent, USA) gel system.

Gene Expression Analysis

The gene expression analysis of the whole genome was carried out using the "Illumina Human-6 v1 Beadchip array system." Through the use of bead-based technology, the microarray used in the present invention evaluated the expression of 47,000 transcripts (Illumina, Inc.). The good-quality RNA (ratio 28S/18S>1.8, RNA Integrity Number>9) was subsequently processed using said standard Illumina protocol. After labelling and hybridization of the sample, the arrays were read using the "Illumina BeadArray Reader." Data were extracted using "Illumina BeadStudio" software. The remaining steps were carried out using the "R" software (The Comprehensive R Archive Network) and its extension to the analysis of the genomic data using "Bioconductor" software. At the time of analysing the data, an updated version of the "Illumina Human-6 v2 Beadchip array" was installed. This new version includes a substantial redesign of the probe sequence and, therefore, the microarray analysis was limited to the portion of the probes considered "valid" according to the new microarray version (data available from Illumina, Inc.). The final expression values of 17,454 transcripts were converted to log2 and normalised using the quantile normalisation method (Bolstad Bioinformatics '03). Before carrying out any statistical analysis, a hierarchical clustering was performed to detect and rule out any possible microarray with extreme values ("outlier").

Construction of the Predictor, Response and Validation

Before applying any modelling technique, the data set obtained from the microarray was filtered for the purpose of excluding non-informative genes. The probes which gave gene expression values below the fifth percentile of the global expression values were considered not expressed and ruled out (N=4, 150). Probes with low variability (variation coefficient<0.03) were also eliminated (n=14,701).

The construction process of a gene expression predictor can be divided into two main steps. Firstly, a good estimation of the predictor's generalisation capacity is required, i.e. the level of reliability that can be expected from the predictor in the future. The adequate way to estimate this measurement is to have an independent validation system which has never been used in the predictor construction process (Ntzani Lancet 2005). Secondly, an impartial selection (not skewed) of the best classification model parameters must be made. This is generally achieved by carrying out a cross-validation analysis. In this case, it is essential to avoid skew when selecting the genes by selecting the set of predictor genes in each of the rounds of crossed-validation (i.e. a full cross-validation must be carried out). Finally, selection of the optimum model from among the apparently good models (i.e. those with a similar and low error rate) must be made on the basis of a confidence measurement rather than arbitrarily.

In the present invention, a predictor of response to treatment with infliximab was built and evaluated taking into account these two preceding steps. The original data, consisting of thirty-six responsive patients and seven non-responsive patients, were randomly divided into a validation group and a test group. The validation group consisted of one-third of the data (two non-responsive patients and twelve responsive patients) and the test group consisted of the remaining two-thirds (five non-responsive patients and twenty-four responsive patients).

In the present invention the "Bioconductor MLInterfaces" library (www.bioconductor.org) was used, which allows fast comparison between the different selections of genes and classifiers. The methods explored were "Diagonal Linear Discriminate Analysis", "Support Vector Machines", "k-Nearest Neighbours (kNN)" and "Random Forests." The discriminated gene sets were selected based on their statistical significance in an F-ratio test. For each method, different numbers of discriminated genes and error prediction by means of LOOCV (Leave-One-Out-Cross-Validation) were tested. Of all the methods tested, the kNN method gave the lowest error rates for several parameter combinations.

With the objective of selecting among multigenic predictors with similar and good performance, the P permutation value was calculated for the significance of each of the models. After a high level of permutations (n=10,000), a P permutation value was obtained by calculating the proportion of statistical significances of the permutation that exceeded the original statistical significances.

Finally, after selecting the optimum prediction model, it was applied to the validation set to estimate predictor reliability. The intervals were calculated using a confidence level of 95% for prediction of reliability using the bootstrap percentile (n=10,000 repetitions).

Gene Expression Patterns

One of the most powerful consequences which can be drawn from the genome expression data is its potential for classifying disease subtypes (van't Veer et al. Nature 2002). By calculating relative distances between individuals and/or genes, groups can be created to show new and unsuspected disease mechanisms. In the present invention, a hierarchical grouping of all the transcripts (mRNA) was carried out in all RA-active patients with the objective of discovering specific patterns. However, an aspect generally overlooked in the analysis group is the determination of a confidence measurement related to the group solidity. It can be shown that even with random data, groups can be formed. Therefore, a confidence measurement to verify the solity of the group is essential. A possible way to estimated said stability is to form subset of genes repeatedly based on the original data and implementing the grouping method. If the same groups are systematically identified, it is assured that these patterns are the real ones. In order to apply this analysis in the present invention "clusterStab" software was used, which gives an estimate of statistical "stability" for each of the clusters.

Results

Evaluation of Clinical Response

A total of forty-eight patients were studied from week zero to week fourteen of treatment with infliximab. Of these, four patients did not reach week fourteen due to septic arthritis, heart attack, reaction to the infusion and voluntary abandonment, respectively. Seven patients were considered to show "poor" EULAR response, while ten patients were classified as being "ACR0" responders. The seven non-responsive EULAR patients were ACR0 patients. The detailed evaluation of the rest of the ACR0 patients showed a favourable result for most of the clinical variables. Therefore, they were all included in the responder group.

Construction and Verification of the Microarray Predictor

Figure 1:
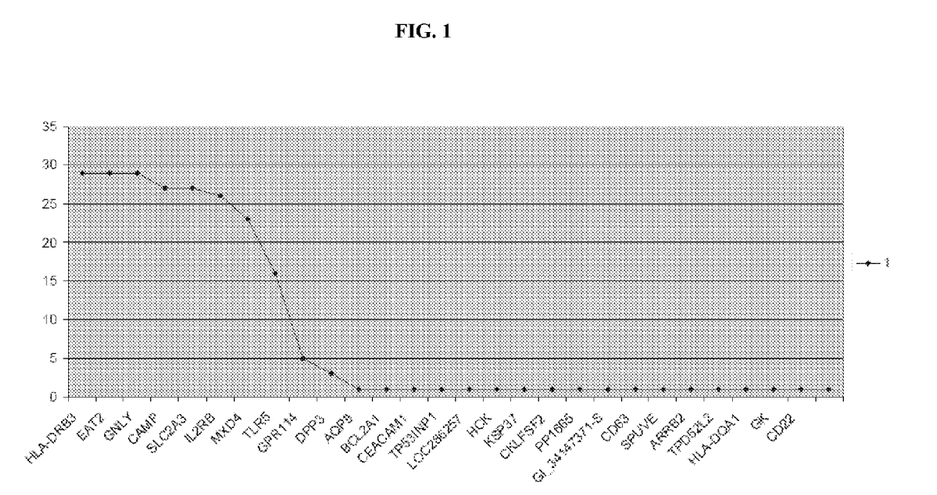
FIG. 1 shows the number of times that each gene is selected from the group of eight genes of the invention, after twenty-nine rounds of LOOCV (Leave-One-Out-Cross-Validation). It can be observed that the group of eight genes of the invention is very frequently selected, while the rest of the genes seem to be subjected to stochastic processes.
Figure 2:
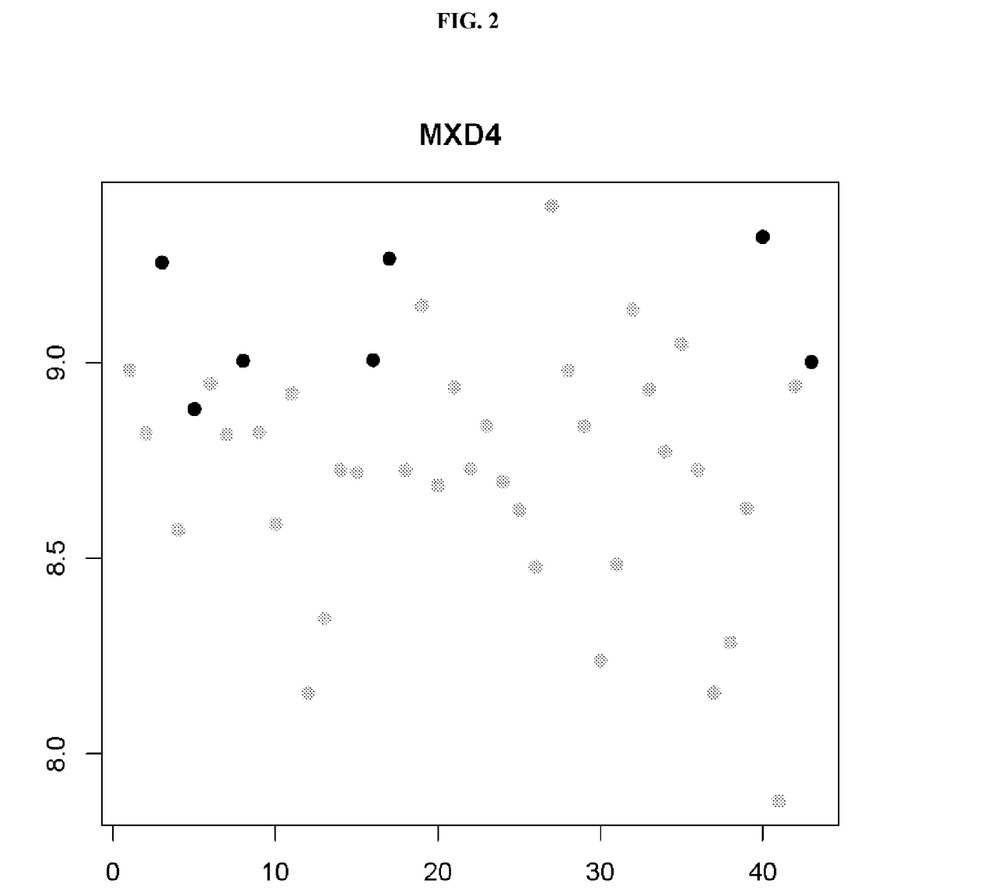
FIG. 2 shows the gene expression profile of MXD4 in forty-three analysed individuals. The black dots correspond to non-responsive patients and the grey dots to responsive patients.
Figure 3:
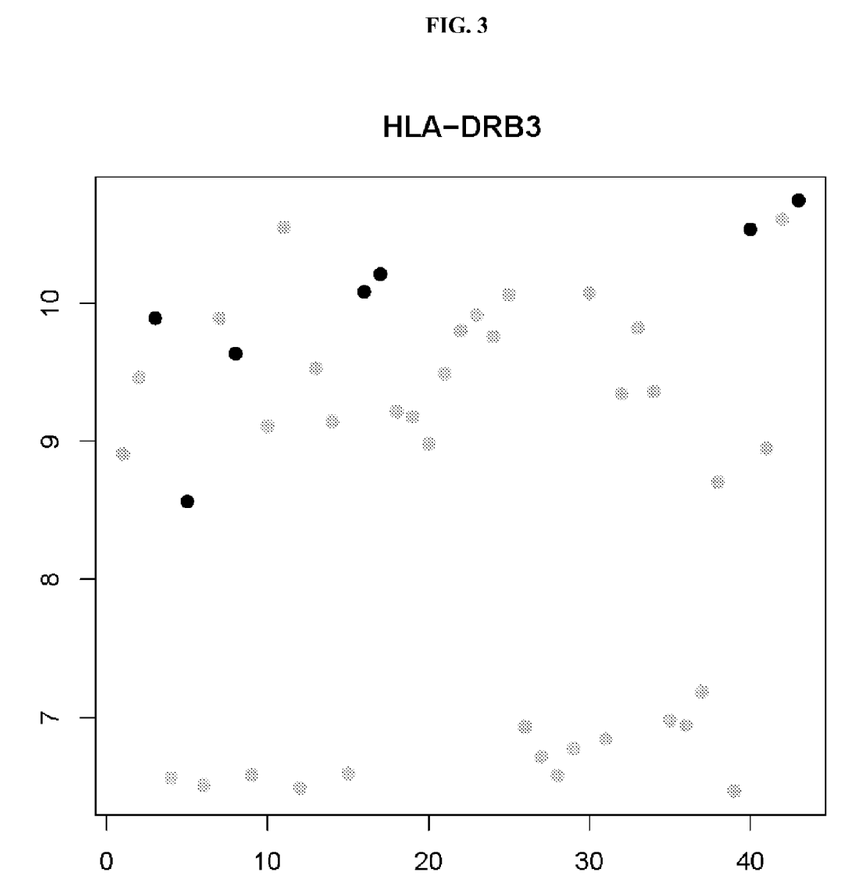
FIG. 3 shows the gene expression profile of HLA-DRB3 in forty-three analysed individuals. The black dots correspond to non-responsive patients and the grey dots to responsive patients.
Figure 4:
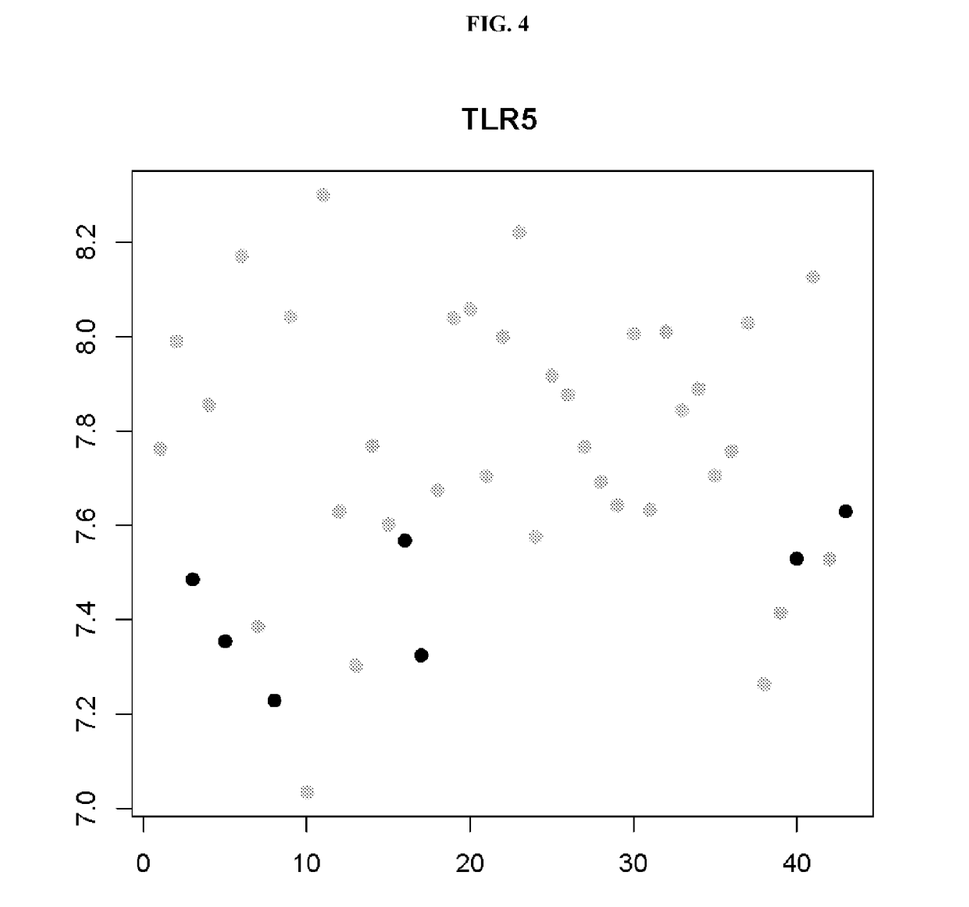
FIG. 4 shows the gene expression profile of TLR5 in forty-three analysed individuals. The black dots correspond to non-responsive patients and the grey dots to responsive patients.
Figure 5:
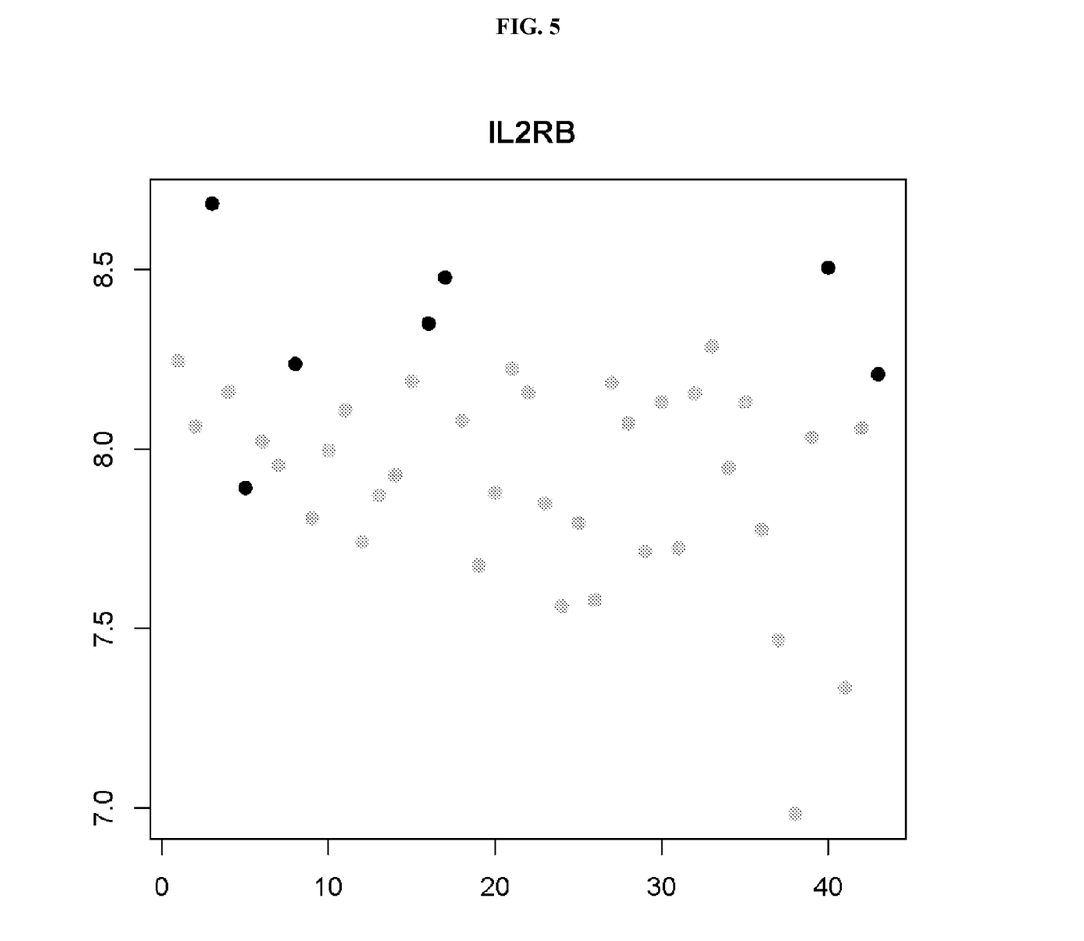
FIG. 5 shows the gene expression profile of IL2RB in forty-three analysed individuals. The black dots correspond to non-responsive patients and the grey dots to responsive patients.
Figure 6:
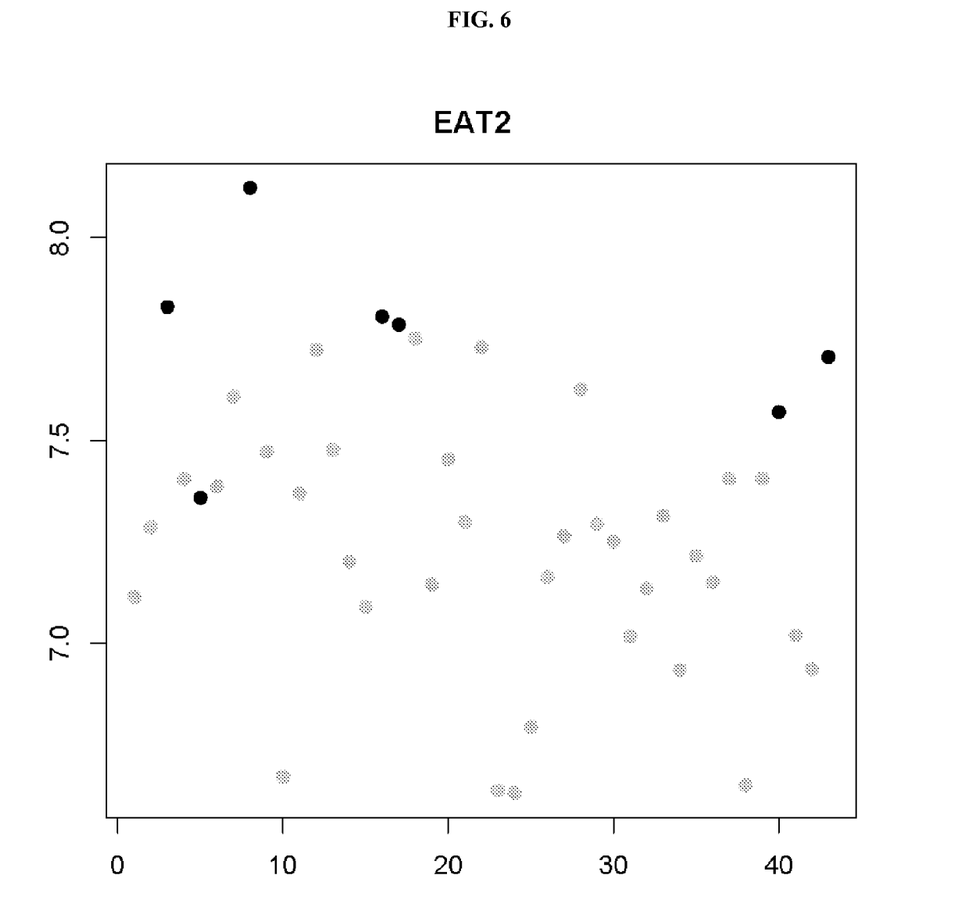
FIG. 6 shows the gene expression profile of EAT2 in forty-three analysed individuals. The black dots correspond to non-responsive patients and the grey dots to responsive patients.
Figure 7:
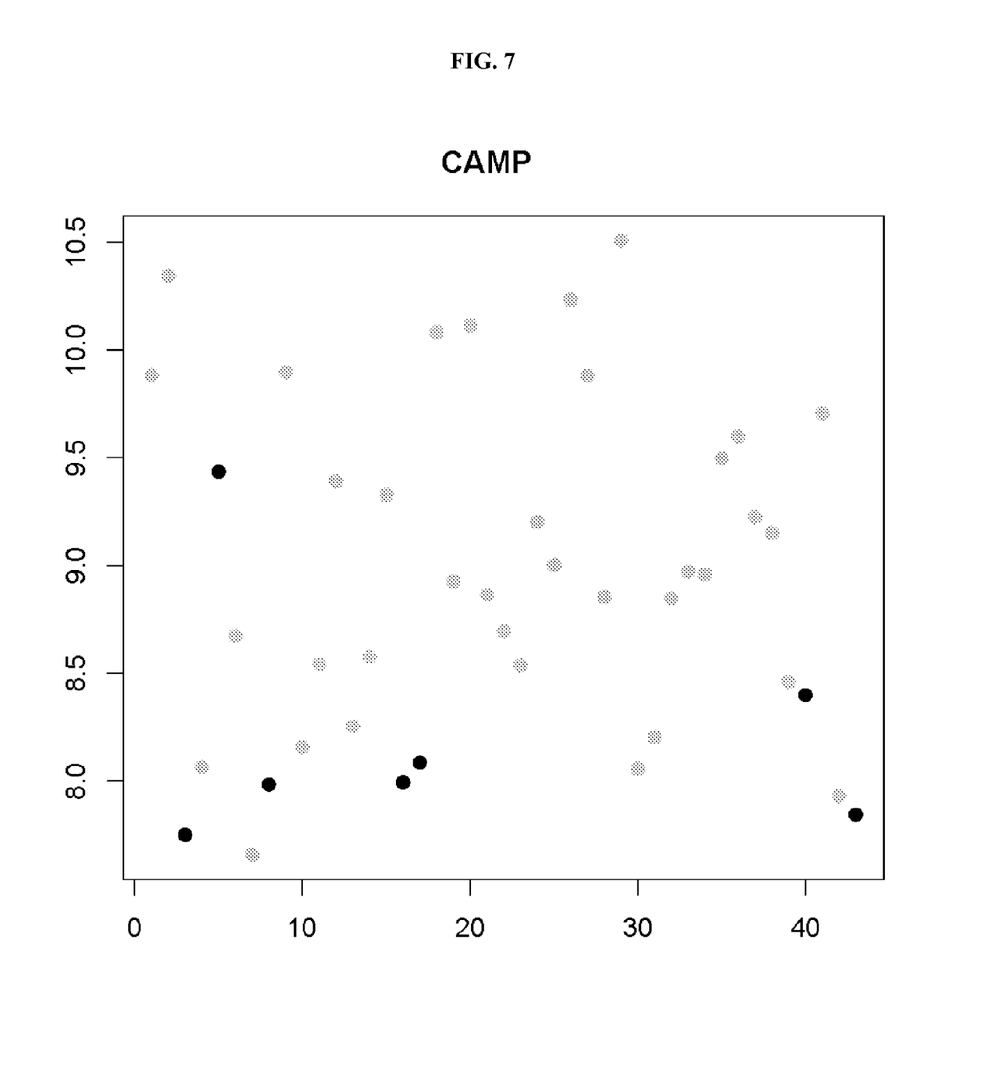
FIG. 7 shows the gene expression profile of CAMP in forty-three analysed individuals. The black dots correspond to non-responsive patients and the grey dots to responsive patients.
Figure 8:
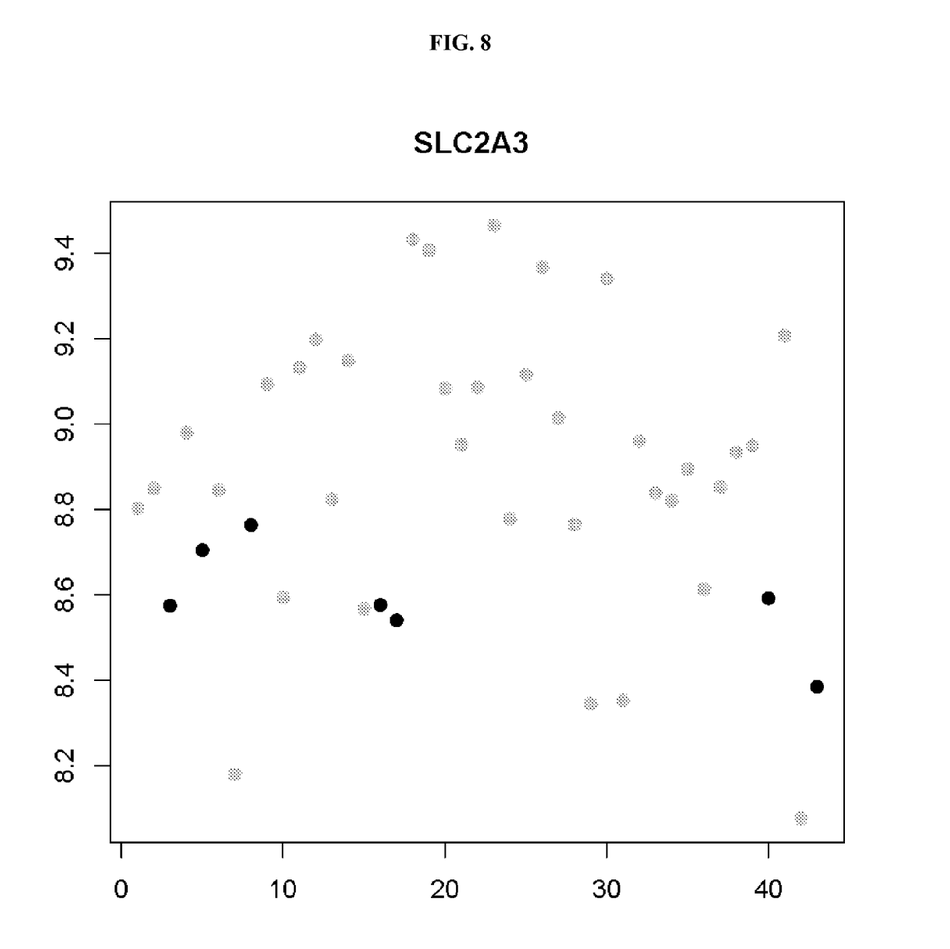
FIG. 8 shows the gene expression profile of SLC2A3 in forty-three analysed individuals. The black dots correspond to non-responsive patients and the grey dots to responsive patients.
Figure 9:
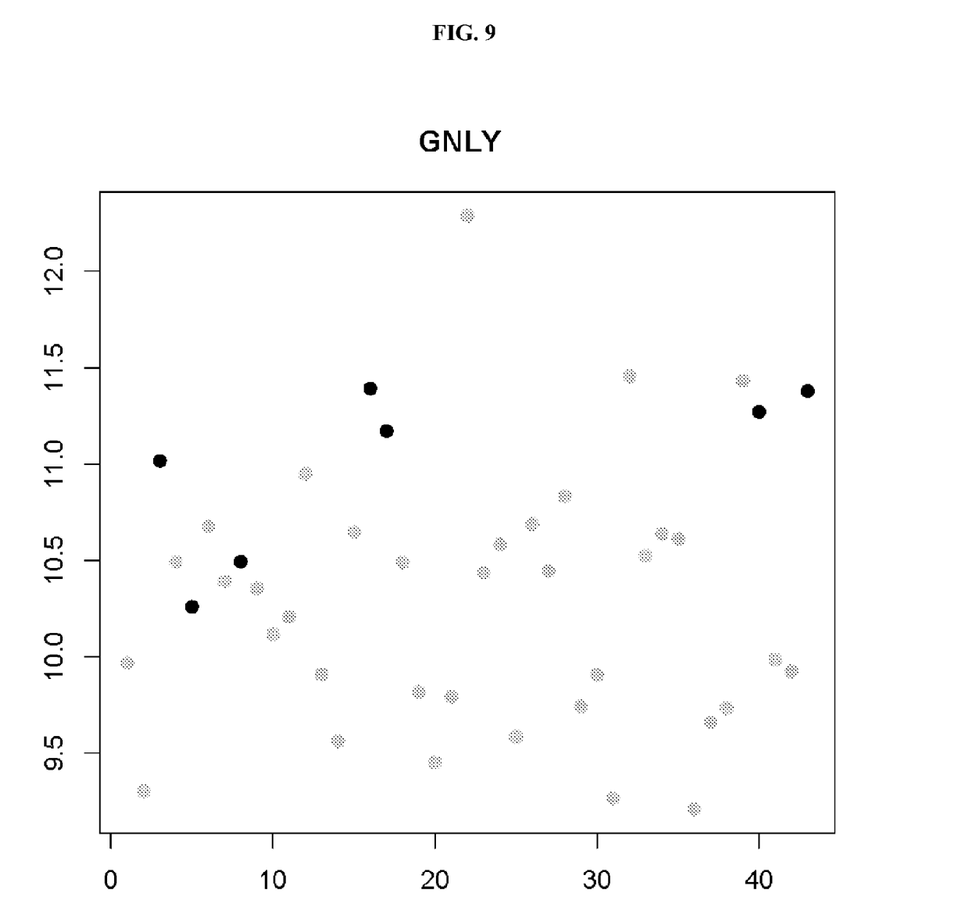
FIG. 9 shows the gene expression profile of GNLY in forty-three analysed individuals. The black dots correspond to non-responsive patients and the grey dots to responsive patients.

The analysis of the hierarchical grouping of normalised data revealed a microarray with a gene expression outside of said grouping and was eliminated from all the analyses. After gene filtration, a total of n=3,364 genes were selected for building the predictor. The kNN classifiers gave the lowest error percentages (only one poor classification out of twenty-nine) for the eight genes of the invention using a model with 3, 4 or 5 nearest neighbours. The frequencies of each of the genes selected through each LOOCV are shown in FIG. 1. The permutation analyses carried out on each of the models identified the 3-NN model as being the most significant (P=0.0001). The application of this prediction model for data validation correctly classified the response to infliximab in twelve of the fourteen individuals (85.7% of prediction precision, 75-100% to 95% IC).

The Hierarchical Grouping

The evaluation of the different numbers of groupings using Jaccard coefficients revealed that the best grouping was made when two main groups were used. In the present invention, a group stability analysis was carried out, revealing that the stability of group 1 was relatively good (86% of stability, 1,000 permutations) compared to an unstable group 2 (40% of stability, 1,000 permutations).

Main Results

Through the use of gene expression profiles in blood samples, a robust multigenic predictor was built for estimating RA patient response to infliximab. The predictor showed a very good percentage of accuracy prediction (86%) in an independent data set. Differences were also identified between T CD4+CD25+ lymphocyte levels in responders compared to non-responders in week zero of the treatment, observing a significantly statistical increase in this cell compartment in the responders (P=0.0009).

Non-responsive patients express higher levels of MXD4, HLA-DRB3, IL2RB, EAT2 and GNLY. These genes could probably suggest an increase in the activity of CD4+CD25+ cells, NK cells, T CD8+ or APC lymphocytes. On the other hand, the over-expressed genes in responsive patients are: TLR5, CAMP, and SLC2A3.

The invention claimed is:

1. A method for treating rheumatoid arthritis in a patient, said method comprising:
   detecting in a sample from the patient the expression level of at least one of the eight genes selected from the group consisting of: HLA-DRB3, EAT2, GNLY, CAMP, SLC2A3, IL2RB, MXD4, and TLR5; and
   administering a TNF-α factor blocking agent to the patients which show over-expression of at least one of the genes selected from the group consisting of TLR5, CAMP and SLC2A3; and not administering the TNF-α factor blocking agent to patients which over-express at least one of the genes selected from the group consisting of MXD4, HLA-DRB3, IL2RB, EAT2, and GNLY, wherein the over-expression is based on the comparison of the expression level of the at least one of the eight genes and the expression values obtained from TNF-α factor blocking agent responsive and TNF-α factor blocking agent non-responsive patients.

2. The method, according to claim 1, which comprises the detection of the overall expression level of the group of eight genes consisting of:
   HLA-DRB3, EAT2, GNLY, CAMP, SLC2A3, IL2RB, MXD4 and TLR5.

3. The method, according to claim 1, which comprises the detection of the expression level of any combination of two or more genes of the group of eight genes selected from the group consisting of: HLA-DRB3, EAT2, GNLY, CAMP, SLC2A3, IL2RB, MXD4, and TLR5.

4. The method, according to claim 1, which comprises the detection of the expression level of at least one of the six genes selected from the group consisting of: HLA-DRB3, EAT2, GNLY, CAMP, IL2RB, and TLR5.

5. The method, according to claim 4, which further comprises the detection of the expression level of at least one of the genes: SLC2A3, MXD4, or both SLC2A3 and MXD4.

6. The method, according to claim 1, which comprises the detection of the overall expression level of the group of six genes consisting of:
   HLA-DRB3, EAT2, GNLY, CAMP, IL2RB and TLR5.

7. The method, according to claim 6, which further comprises the detection of the expression level of at least one of the genes: SLC2A3, MXD4, or both SLC2A3 and MXD4.

8. The method according to claim 1, wherein the rheumatoid arthritis patients
   (a) fulfill the 1987 ACR (American College of Rheumatology) criteria for rheumatoid arthritis diagnosis and have a DAS28 index >3.2,
   (b) said patients are tolerant to ≤20 mg/week methotrexate,
   (c) said patients are able to receive ≤10 mg/day prednisolane and treatment with NSAID,
   wherein the doses of methotrexate, glucocorticoids and NSAID remaining stable during the four weeks prior to treatment with infliximab or adalimumab and said patients have not received any other DMARD during the four weeks prior to the aforesaid treatment with infliximab or adalimumab.

9. The method according to claim 1, wherein the TNF-α factor blocking agent is selected from infliximab or adalimumab.

10. The method according to claim 1, wherein the expression level is carried out by quantifying mRNA level in a blood sample from the patient.

* * * * *